(12) United States Patent
Chen et al.

(10) Patent No.: US 8,182,830 B2
(45) Date of Patent: May 22, 2012

(54) HYDROGEN SULFIDE GENERATING POLYMERS

(75) Inventors: Mingfei Chen, Santa Rosa, CA (US); Christopher Storment, Sonoma, CA (US); David Shumaker, Sebastopol, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 153 days.

(21) Appl. No.: 12/606,346

(22) Filed: Jan. 5, 2010

(65) Prior Publication Data

US 2011/0165216 A1 Jul. 7, 2011

(51) Int. Cl.
*C08F 20/38* (2006.01)
*A61F 2/00* (2006.01)

(52) U.S. Cl. .............. 424/423; 424/78.36; 526/288; 528/203; 528/321; 528/390

(58) Field of Classification Search .............. 424/423, 424/78.36; 526/288; 528/230, 321, 390
See application file for complete search history.

(56) References Cited

U.S. PATENT DOCUMENTS

| | | | |
|---|---|---|---|
| 4,835,126 | A | 5/1989 | Wachs et al. |
| 5,362,718 | A | 11/1994 | Skotnicki et al. |
| 5,507,848 | A | 4/1996 | Beckman |
| 5,914,162 | A | 6/1999 | Bilkadi |
| 6,015,815 | A | 1/2000 | Mollison |
| 6,270,788 | B1 | 8/2001 | Koulik et al. |
| 6,329,386 | B1 | 12/2001 | Mollison |
| 6,486,214 | B1 * | 11/2002 | Uhrich ............ 514/772.5 |
| 6,500,108 | B1 * | 12/2002 | Sorensen et al. ......... 600/3 |
| 2002/0022046 | A1 | 2/2002 | Tedeschi et al. |
| 2003/0077243 | A1 | 4/2003 | Fitzhugh et al. |
| 2005/0079148 | A1 | 4/2005 | Fitzhugh et al. |
| 2005/0084515 | A1 | 4/2005 | Udipi et al. |
| 2005/0281857 | A1 | 12/2005 | Heyer et al. |
| 2008/0004245 | A1 | 1/2008 | Wallace et al. |
| 2008/0171725 | A1 | 7/2008 | Roth et al. |
| 2008/0187604 | A1 | 8/2008 | Tomaselli et al. |
| 2009/0233888 | A1 | 9/2009 | Lin |

OTHER PUBLICATIONS

Benavides, et. al., Proc. Nat'l. Acad. Sci. USA, 104; 17977-17982 (2007).
Lefer, Proc. Nat'l, Acad. Sci, USA, 104: 17907-17908 (2007).
Rapp et al., "Lipids of Human Atherosclerotic Plaques and Xanthomas; Clues to the Mechanism of Plaque Progression" Journal of Lipid Research, vol. 24, 1983 pp. 1329-1335.
Rothblat et al., "Apolipoproteins, Membrane Cholesterol Domains, and the Regulation of Cholesterol Efflux" Journal of Lipid Research, vol. 33. 1992, pp. 10911097.
Fielding, et al., "Molecular Physiology of Reverse Cholesterol Transport" Journal of Lipid Research, vol. 36, 1995, pp. 211-228.
Badimon et al., "High Density Lipoprotein Plasma Fractions Inhibit Aortic Fatty Streaks in Cholesterol-Fed Rabbits" Lab Invest. Mar. 1989:60(3):455-61.
Miyazaki et al., "Intravenous Injection of Rabbit Apolipoprotein A-I Inhibits the Progression of Atherosclerosis in Cholesterol-Fed Rabbits" Arteriosclerosis, Thrombosis, and Vascular Biology, vol. 15, No. 11, Nov. 1995, pp. 1882-1888.
Brown et al., "Lipid Lowering and Plaque Regression. New Insights into Prevention of Plaque Disruption and Clinical Events in Coronary Disease" Circulation 1993; 87; 1781-1791.
Atger et al., "Cyclodextrins as Catalysts for the Removal of Cholesterol from Macrophage Foam Cells" J. Clin.Invest., vol. 99, No. 4, Feb. 1997, pp. 773-780.
Gressier, J. C. et al. *"Polymer-supported transition-metal complexes. 2. Synthesis and Moessbauer investigation of copolymers containing polynuclear iron carbonyl complexes"*, Macromolecules, 16 (10), 1577-81.
Worral, David E.: *"Action of hydroxylamine and hydrazine on acetylenic thio amides"*, Journal of American Chemical Society, 59, 933-4.
Lefer, David "A New Gaseous Signaling Molcule Emerges: Cardioprotective Role of Hydrogen Sulfide" www.pnas.org/cgi/doi/10.1073/pnas.0709010104, Nov. 13, 2007, vol. 104, No. 46, pp. 17907-17908.

* cited by examiner

*Primary Examiner* — David W Wu
*Assistant Examiner* — Chun-Cheng Wang

(57) ABSTRACT

Described herein are hydrogen sulfide ($H_2S$) generating polymers and polymer systems suitable for coating or forming medical devices and methods for making and using the same. More specifically, described are $H_2S$ generating polymers comprising at least one thioamide group. The $H_2S$ generating polymers can provide controlled site-specific release of $H_2S$ once implanted at or within the target surgical site by hydrolysis of the thioamide group in physiological media. The $H_2S$ generating polymers can be coated onto a medical device, formed into a medical device or combined with one or more other polymers to form a polymer system. Also described are methods of treating restenosis and inflammation and promoting vasodilation utilizing such medical devices.

14 Claims, 1 Drawing Sheet

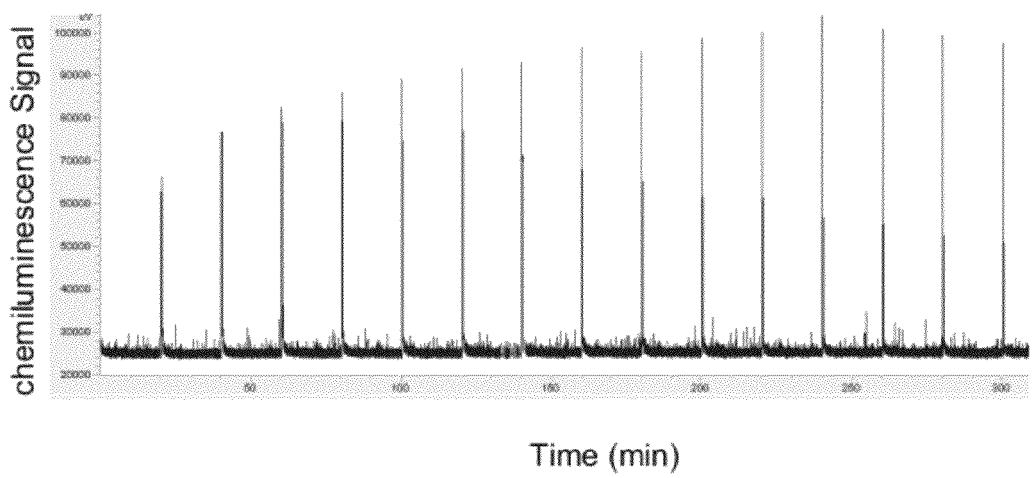

HYDROGEN SULFIDE GENERATING POLYMERS

FIELD OF THE INVENTION

The present invention relates to hydrogen sulfide ($H_2S$) generating polymers for fabricating and coating medical devices.

BACKGROUND OF THE INVENTION

For years, research in cardiovascular medicine has focused on the delivery of nitric oxide (NO) and carbon monoxide (CO), both of which are endogenously produced diatomic signaling molecules. It has been determined that therapies based on the administration of CO and NO protect the brain, heart and circulation against any number of cardiovascular diseases and conditions.

However, several studies have shown that both CO and NO treatments can be less than beneficial to a recipient. Although CO is beneficial for certain therapies, it has been known for decades to be a poisonous chemical in excess as it competes with carbon dioxide ($CO_2$) for preferential binding to hemoglobin in the blood. This preferential binding of CO leads to an excess of $CO_2$ in the blood and a detrimental state for the individual. NO, on the other hand, has been shown to be toxic at high concentrations due to the highly reactive nature of NO and its interaction with superoxide to form the potent oxidant peroxynitrite ($ONOO^-$).

As a result of the two diatomic signaling molecule's acute toxicities, site specific administration has been pursued over the last decade, particularly of NO. Implantable medical devices such as vascular stents have been developed incorporating coatings which can provide controlled release of NO once implanted into a diseased vessel. This site-specific administration of NO avoids the toxicity of a systemic administration, but does not avoid the effects of local $ONOO^-$ formation.

Recently, a third endogenously produced signaling molecule, hydrogen sulfide ($H_2S$), has emerged as a candidate for cardiovascular therapy. Studies have shown that $H_2S$ may be beneficial for vasodilatation, anti-inflammation, anti-restenosis and therapeutic angiogenesis. See Benavides, et. al., Proc. Nat'l. Acad. Sci. USA, 104: 17977-17982 (2007) and Lefer, Proc. Nat'l. Acad. Sci. USA, 104: 17907-17908 (2007), the contents of which are incorporated herein in their entirety. However, $H_2S$ by nature is a toxic gas and, therefore, systemic administration is not a viable means for treating cardiovascular conditions. Therefore, methods of local, site-specific, administration of $H_2S$ in order to utilize its vasodilating, anti-inflammation, anti-restenotic and therapeutic angiogenic properties would be highly beneficial.

SUMMARY OF THE INVENTION

Described herein are hydrogen sulfide ($H_2S$) generating polymers suitable for fabricating and coating medical devices and methods of making and using the same. More specifically, $H_2S$ generating polymers are described comprising functional groups that can react under physiological conditions to generate $H_2S$ in a controlled manner.

Further described herein are hydrogen sulfide ($H_2S$) generating polymers comprising at least one thioamide group. In one embodiment, the polymer may be selected from the group consisting of polyesters, vinyl polymers, ether-ester polymers, polyanhydrides, phosphoester polymers, polyamines, polyamides, polyimines, polyimides, acrylic polymers, polycarbonates, polyolefins, polyurethanes, combinations and derivatives thereof. The thioamide group may be present as part of the polymer backbone (e.g. as a polythioamide) or as part of a pendant group.

While it is known that a thioamide group of a small molecule may be hydrolyzed to generate hydrogen sulfide, it is surprising that thioamide groups on macromolecules such as polymers also hydrolyze with ease and, more surprisingly, that a thioamide-comprising polymer coating on a metallic surface, such as might be found on an implantable medical device, generates therapeutic quantities of hydrogen sulfide when subjected to physiological conditions.

Yet further described herein are hydrogen sulfide generating polymers comprising: at least one monomer unit having a structure of Formula 1, Formula 2 or Formula 3:

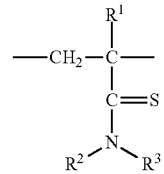

Formula 1

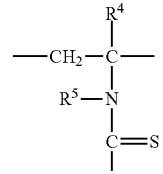

Formula 2

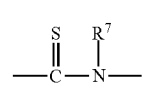

Formula 3 wherein each of $R^1$ through $R^7$ is independently selected from hydrogen, $C_1$ to $C_{25}$ straight chain alkyl, $C_3$ to $C_8$ cyclic alkyl, or $C_3$ to $C_{25}$ branched alkyl, or any combination thereof, and $R^2$ and $R^3$ taken together and $R^5$ and $R^6$ taken together are each independently —$(CH_2)$—$_m$, wherein m is an integer of from 3 to 5.

In another embodiment, the $H_2S$ generating polymer further comprises one or more additional monomer units selected from the group consisting of methyl methacrylate, butyl methacrylate, hexyl methacrylate, ethyl methacrylate, 2-ethoxyethyl methacrylate, methyl acrylate, ethyl acrylate, hexyl acrylate and butyl acrylate.

Further described herein are implantable medical devices comprising a hydrogen sulfide generating polymer. In one embodiment, the hydrogen sulfide generating polymer comprises at least one monomer unit of Formula 1, Formula 2 or Formula 3.

In one embodiment the implantable medical devices further comprise one or more additional monomer units selected from the group consisting of methyl methacrylate, butyl methacrylate, hexyl methacrylate, ethyl methacrylate, 2-(ethoxy ethylmethacrylate), methyl acrylate, ethyl acrylate, hexyl acrylate and butyl acrylate.

In yet another embodiment, the implantable medical device is selected from the group consisting of stents, catheters, micro-particles, probes, vascular grafts, and combinations thereof. In one embodiment the implantable medical device comprises a stent, preferably a vascular stent. In another embodiment, the implantable medical device further comprises a primer layer. In still another embodiment, the implantable medical device further comprises a cap coat. The cap coat may comprise a porous biostable polymer, such that water molecules from the physiological medium may diffuse to the thioamide polymer to allow for the generation of $H_2S$, or may comprise a biodegradable polymer which, upon degradation, exposes the thioamide polymer to the physiological medium.

In further embodiments, the $H_2S$ generating polymer comprises one or more additional bioactive agents. In another embodiment, the one or more additional bioactive agent is selected from the group consisting of anti-proliferatives, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, anti-sense nucleotides and transforming nucleic acids. cytostatic compounds, toxic compounds, chemotherapeutic agents, analgesics, antibiotics, protease inhibitors, statins, nucleic acids, polypeptides, growth factors and delivery vectors, liposomes, and combinations thereof. In one embodiment the additional bioactive agent is rapamycin, a rapamycin analog such as zotarolimus or everolimus, or paclitaxel.

In one embodiment, described is an $H_2S$ generating vascular stent comprising: a stent; and a polymer coating disposed upon the stent wherein the polymer comprises at least one monomeric unit of Formula 1, Formula 2 or Formula 3. In another embodiment, the stent further comprises a primer coating disposed on said stent. In still another embodiment, the stent further comprises a cap coat disposed on the stent. In another embodiment, described is an $H_2S$ generating vascular stent having a stent body comprising a polymer, wherein the polymer comprises at least one monomeric unit of Formula 1, Formula 2 or Formula 3.

In further embodiments are described methods for inhibiting restenosis, inhibiting inflammation and promoting vasodilation by site-specific generation of $H_2S$ utilizing an $H_2S$ generating vascular stent as described above.

BRIEF DESCRIPTION OF THE DRAWINGS

FIG. 1 is a chemiluminescence graph illustrating $H_2S$ release over time, in one example of the present invention.

DEFINITION OF TERMS

Certain terms as used in the specification are intended to refer to the following definitions, as detailed below. Where the definition of terms departs from the commonly used meaning of the term, applicant intends to utilize the definitions provided below, unless specifically indicated.

Compatible: As used herein, "compatible" refers to a composition possessing the optimum, or near optimum combination of physical, chemical, biological and drug release kinetic properties suitable for a controlled-release coating made in accordance with the teachings of the present disclosure. Physical characteristics include durability and elasticity/ductility, chemical characteristics include solubility and/or miscibility and biological characteristics include biocompatibility. The drug release kinetic should be either near zero-order or a combination of first and zero-order kinetics.

Controlled release: As used herein "controlled release" refers to the release of a bioactive compound from a medical device surface at a predetermined rate. Controlled release implies that the bioactive compound does not come off the medical device surface sporadically in an unpredictable fashion and does not "burst" off of the device upon contact with a biological environment (also referred to herein a first order kinetics) unless specifically intended to do so. However, the term "controlled release" as used herein does not preclude a "burst phenomenon" associated with deployment. In some embodiments an initial burst of drug may be desirable followed by a more gradual release thereafter. The release rate may be steady state (commonly referred to as "timed release" or zero order kinetics), that is the drug is released in even amounts over a predetermined time (with or without an initial burst phase) or may be a gradient release. A gradient release implies that the concentration of drug released from the device surface changes over time.

Copolymer: As used herein, a "copolymer" will be defined as a macromolecule produced by the simultaneous chain addition polymerization of two or more dissimilar units such as monomers. Copolymer shall include bipolymers (two dissimilar units), terpolymers (three dissimilar units), etc.

Glass Transition Temperature ($T_g$): As used herein "glass transition temperature" or $T_g$ refers to a temperature wherein a polymer structurally transitions from an elastic pliable state to a rigid and brittle state.

$M_n$: As used herein, $M_n$ refers to number-average molecular weight. Mathematically it is represented by the following formula:

$$M_n = \Sigma_i N_i M_i / \Sigma_i N_i, \text{ wherein the } N_i \text{ is the number of moles whose weight is } M_i.$$

$M_w$: As used herein, $M_w$ refers to weight average molecular weight that is the average weight that a given polymer may have. Mathematically it is represented by the following formula:

$$M_w = \Sigma_i N_i M_i^2 / \Sigma_i N_i M_i, \text{ wherein } N_i \text{ is the number of molecules whose weight is } M_i.$$

DETAILED DESCRIPTION OF THE INVENTION

Described herein are hydrogen sulfide ($H_2S$) generating polymers and polymer systems suitable for coating or forming medical devices and methods for making and using the same. More specifically, $H_2S$ generating polymers are described comprising at least one thioamide group. Suitable polymers include polyesters, vinyl polymers, ether-ester polymers, polyanhydrides, phosphoester polymers, polyamines, polyamides, polyimines, polyimides, acrylic polymers, polycarbonates, polyolefins, polyurethanes, and combinations and derivatives thereof.

While it is known that a thioamide group of a small molecule may be hydrolyzed to generate hydrogen sulfide, it is surprising that thioamide groups on macromolecules such as polymers also hydrolyze with ease and, more surprisingly, that a thioamide-comprising polymer coating on a metallic surface, such as might be found on an implantable medical device, generates therapeutic amounts of hydrogen sulfide when subjected to physiological conditions.

Further, $H_2S$ generating polymers, such as those listed above, are described comprising at least one monomer unit with at least one thioamide group. The $H_2S$ generating polymers provide controlled release of $H_2S$ once implanted at or within the target site by means of hydrolysis of the thioamide group in a physiological medium, and can be coated onto a medical device, formed into a medical device, or combined with one or more other polymers to form a polymer system suitable for the same.

In one embodiment, an exemplary $H_2S$ generating polymer comprises at least one monomer unit of Formula 1, Formula 2 or Formula 3.

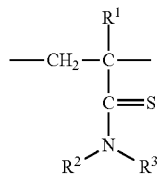

Formula 1

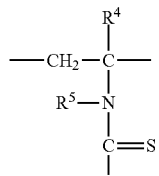

Formula 2

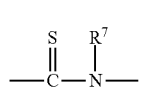

Formula 3 wherein each of $R^1$ through $R^7$ is independently selected from hydrogen, $C_1$ to $C_{25}$ straight chain alkyl, $C_3$ to $C_8$ cyclic alkyl, or $C_3$ to $C_{25}$ branched alkyl, or any combination thereof, and $R^2$ and $R^3$ taken together and $R^5$ and $R^6$ taken together are each independently $-(CH_2)-_m$, wherein m is an integer of from 3 to 5.

In one embodiment, $H_2S$ generating polymers can comprise a monomer unit of Formula 1, Formula 2 or Formula 3 and at least one additional monomer unit, preferably an acrylate monomer unit such as, but not limited to, methyl methacrylate, methyl butylmethacrylate, butyl methacrylate, hexyl methacrylate, ethyl acrylate, 2-ethoxyethyl methacrylate, methyl acrylate, ethyl acrylate, hexyl acrylate and butyl acrylate. In another embodiment, the polymer may comprise only monomer units of Formula 1, Formula 2 and/or Formula 3 either as copolymers or as homopolymers.

In one embodiment, described is an $H_2S$ generating vascular stent comprising: a stent; and a polymer coating disposed upon the stent wherein the polymer comprises at least one monomeric unit of Formula 1, Formula 2 or Formula 3. In another embodiment, the stent further comprises a primer coating disposed on said stent. In still another embodiment, the stent further comprises a cap coat disposed on the stent. In another embodiment, described is an $H_2S$ generating vascular stent having a stent body comprising a polymer, wherein the polymer comprises at least one monomeric unit of Formula 1, Formula 2 or Formula 3.

In one embodiment the $H_2S$ generating polymer is a copolymer of a thioamide and an acrylate, represented by Formula 4

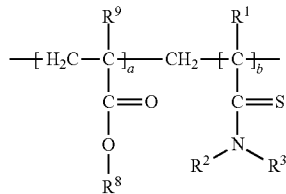

wherein $R^1$, $R^2$ and $R^3$ are as above. $R^9$ is hydrogen or $C_1$ to $C_8$ alkyl, $R^8$ is $C_1$ to $C_8$ alkyl, and a and b are each independently an integer of from 1 to 5,000, with the ratio of a:b between about 1:100 to about 100:1.

In another embodiment the $H_2S$ generating polymer is another copolymer of a thioamide and an acrylate, represented by Formula 5

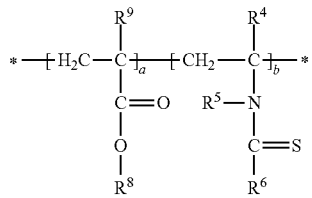

Formula 5 wherein $R^4$, $R^5$, $R^6$, $R^8$, $R^9$, a and b and the ratio of a to b are as above.

In another embodiment the $H_2S$ generating polymer is a terpolymer of a thioamide, an acrylate and a vinyl ester, represented by Formula 6

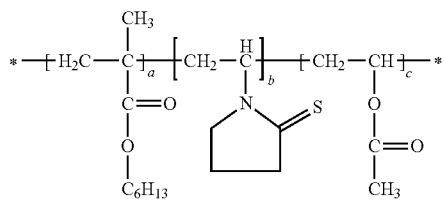

Formula 6 wherein a and b are as above and c is an integer of from 1 to 5,000, and the ratio of a:b:c is between about 1:100:1 and 100:1:100.

The thioamide group on all of the above-described polymers is readily hydrolyzed in the presence of water in a physiological environment such as blood to generate hydrogen sulfide, as depicted in the following reaction:

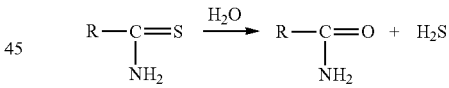

wherein R represents the balance of the polymer molecule.

The thioamide-comprising $H_2S$ generating polymers are prepared from the corresponding amide-comprising polymers by reaction, for example, with Lawesson's reagent, (2,4-bis(4-methoxyphenyl)-1,3,2,4-dithiadiphosphetane-2,4-disulfide), at an elevated temperature in an inert organic solvent such as toluene, as depicted in the exemplary reaction below:

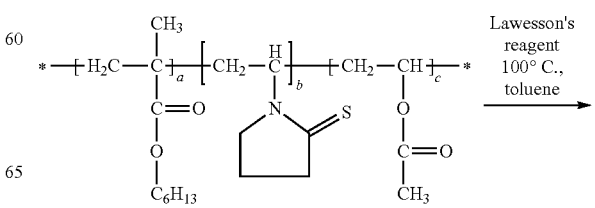

Lawesson's reagent
100° C.,
toluene

-continued

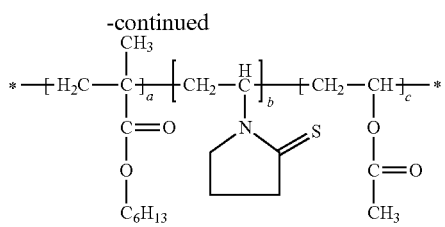

Physical properties of the H₂S generating polymers described herein can be fine tuned to optimally perform for their intended use. Properties that can be fine tuned, without limitation, include $T_g$, molecular weight (both $M_n$ and $M_w$), polydispersity index (PDI, the quotient of $M_w/M_n$), degree of elasticity and degree of amphiphilicity. In one embodiment, the $T_g$ of the polymers range from about −10° C. to about 85° C. In still another embodiment, the PDI of the polymers range from about 1.35 to about 4. In another embodiment, the $T_g$ of the polymers ranges form about 0° C. to about 40° C. In still another embodiment, the PDI of the polymers range from about 1.5 to about 2.5.

In an exemplary embodiment, the H₂S generating polymeric coatings described herein are used to coat medical devices deployed in a hemodynamic environment. As such, in some embodiments, the H₂S generating polymers possess excellent adhesive properties. That is, the coating has the ability to be stably coated on the medical device surface.

The medical devices used may be permanent medical implants, temporary implants, or removable devices. For example, and not intended as a limitation, the medical devices may include stents, catheters, micro-particles, probes, and vascular grafts.

In one embodiment, the medical device is a stent or stents. The stents may be vascular stents, urethral stents, biliary stents, or stents intended for use in other ducts and organ lumens. Vascular stents, for example, may be used in peripheral, cerebral, or coronary applications. The stents may be rigid expandable stents or pliable self-expanding stents. Many different materials can be used to fabricate the implantable medical devices including, but not limited to, stainless steel, nitinol, aluminum, chromium, titanium, gold, cobalt, alloys of the above, ceramics, and a wide range of synthetic polymeric and natural materials including, but not limited to, collagen, fibrin and plant fibers. All of these materials, and others, may be used with the polymeric coatings made in accordance with the teachings disclosed herein. Furthermore, the H₂S generating polymers described herein can be used to fabricate an entire medical device.

The stents may also be bioresorbable. In one embodiment, vascular stents are implanted into coronary arteries immediately following angioplasty. In another embodiment, vascular stents are implanted into the abdominal aorta to treat an abdominal aneurysm.

In another embodiment, the H₂S generating polymeric coatings are non-bioresorbable or substantially non-bioresorbable. A "non-bioresorbable" H₂S generating polymeric coating as used herein is biocompatible and not subject to breakdown in vivo through the action of normal biochemical pathways. In one embodiment, the H₂S generating polymeric coatings are substantially non-bioresorbable and remain greater than 95% intact after 1 year of implantation. In other embodiments, the substantially non-bioresorbable H₂S generating polymeric coatings remain greater than 90% intact after 1 year.

In another embodiment, the H₂S generating polymeric coatings are bioresorbable, meaning the H₂S generating polymeric coatings are biocompatible and are broken down in vivo through the action of normal biochemical pathways. In one embodiment, the H₂S generating polymeric coatings are bioresorbable and remain less than 5% intact after 1 year of implantation. In other embodiments, the H₂S generating polymeric coatings are bioresorbable and remain less than 5% intact after 2 years of implantation. In other embodiments, the H₂S generating polymeric coatings are bioresorbable and remain less than 5% intact after 5 years of implantation.

The H₂S generating polymers and associated polymeric coatings described herein can be formed as linear or branched polymers. Additionally, the polymers themselves can be formed as thermosets in order to attain a specific shape.

Further, the H₂S generating polymers and associated polymeric coatings described herein can be formed as a copolymer with one or more other monomers. The copolymer can be randomly assembled or can be a block copolymer wherein the polymer is formed with blocks of various monomers. One skilled in the art understands that copolymers can be fine tuned depending on, for example, monomer ratios, number of different monomers used (e.g. biopolymer, terpolymer), monomer hydrophobicity or hydrophilicity, monomer molecular weight, polymer molecular weight, catalyst used and polymerization temperature.

There are many theories that attempt to explain, or contribute to our understanding of how polymers adhere to surfaces. The most important forces include electrostatic and hydrogen bonding. However, other factors including wettability, absorption and resiliency also determine how well a polymer will adhere to different surfaces. Therefore, polymer base coats, or primers are often used in order to create a more uniform coating surface.

The H₂S generating polymeric coatings described herein can be applied to medical device surfaces, either primed or bare, in any manner known to those skilled in the art. Application methods for the H₂S generating polymeric coatings include, but are not limited to, spraying, dipping, brushing, vacuum-deposition, and the like. Moreover, in some embodiments, the H₂S generating polymeric coatings may be used with a cap coat. A cap coat as used herein refers to the outermost coating layer applied over another coating.

In one embodiment, a primer coating is applied to the surface of a stent or other implantable medical device. Then a H₂S generating polymer coating is applied over the primer coat. Thereafter, a polymer cap coat may optionally be applied over the H₂S generating polymeric coating. The cap coat may optionally serve as a diffusion barrier to control the H₂S release. The cap coat may be merely a biocompatible polymer applied to the surface of the sent to protect the stent and have no effect on the H₂S release rates. The cap coat may comprise a porous biostable polymer, such that water molecules from the physiological medium may diffuse to the thioamide polymer to allow for the generation of H₂S, or may comprise a biodegradable polymer which, upon degradation, exposes the thioamide polymer to the physiological medium.

The H₂S generating polymeric coating may further comprise one or more bioactive agents. The choice of bioactive agent to incorporate, or how much to incorporate, will have a great deal to do with the polymer selected to coat or form the implantable medical device. A person skilled in the art will appreciate that hydrophobic agents prefer hydrophobic polymers and hydrophilic agents prefer hydrophilic polymers. Therefore, coatings and medical devices can be designed for agent or agent combinations with immediate release, sustained release or a combination of the two.

Exemplary, non limiting examples of bioactive agents that can be incorporated into the polymers and polymeric coating presently described include anti-proliferatives including, but not limited to, macrolide antibiotics including FKBP-12 binding compounds, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, anti-sense nucleotides and transforming nucleic acids. Drugs can also refer to bioactive agents including anti-proliferative compounds, cytostatic compounds, toxic compounds, anti-inflammatory compounds, chemotherapeutic agents, analgesics, antibiotics, protease inhibitors, statins, nucleic acids, polypeptides, growth factors and delivery vectors including recombinant micro-organisms, liposomes, and the like.

Exemplary FKBP-12 binding agents include sirolimus (rapamycin), tacrolimus (FK506), everolimus (certican or RAD-001), temsirolimus (CCI-779 or amorphous rapamycin 42-ester with 3-hydroxy-2-(hydroxymethyl)-2-methylpropionic acid as disclosed in U.S. patent application Ser. No. 10/930,487) and zotarolimus (ABT-578; see U.S. Pat. Nos. 6,015,815 and 6,329,386). Additionally, other rapamycin hydroxyesters as disclosed in U.S. Pat. No. 5,362,718 may be used in combination with the polymers described herein.

In one embodiment the polymer chosen for a cap coat is preferably a polymer that is biocompatible and minimizes irritation to the vessel wall when the medical device is implanted. The polymer may be either a biostable, bioabsorbable or bioresorbable polymer depending on the desired rate of release or the desired degree of polymer stability. Bioabsorbable polymers that can be used include poly(L-lactic acid), polycaprolactone, poly(lactide-co-glycolide), poly(ethylene-vinyl acetate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly(ether-esters) (e.g. PEO/PLA), polyalkylene oxalates, polyphosphazenes and biomolecules such as fibrin, fibrinogen, cellulose, starch, collagen and hyaluronic acid.

Also, biostable polymers with a relatively low chronic tissue response such as polyurethanes, silicones, and polyesters could be used and other polymers could also be used if they can be dissolved and cured or polymerized on the medical device such as polyolefins, polyisobutylene and ethylene-alphaolefin copolymers; acrylic polymers and copolymers, ethylene-co-vinylacetate, polybutylmethacrylate, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins, polyurethanes; rayon; rayon-triacetate; cellulose, cellulose acetate, cellulose butyrate; delivery of a therapeutic dosage of hydrogen sulfide by release from an implantable medical device comprising a hydrogen sulfide generating polymer. In a preferred embodiment the implantable medical device is a vascular stent.

The "therapeutic dosage" of hydrogen sulfide released in a controlled site-specific manner from an implantable medical device comprising a hydrogen sulfide generating polymer, is that dosage that is the same or similar to the dosage produced by the enzymatic endogenous release of hydrogen sulfide in mammals, as discussed in Lefer, cited above, and references cited therein, all of which are incorporated herein in their entirety. Such dosage, typically in the micromolar range, is therapeutically effective for inhibiting restenosis, inhibiting inflammation and/or promoting vasodilation without causing substantial side effects or harm.

EXAMPLES

The following Examples are intended to illustrate non-limiting processes for preparing hydrogen sulfide generating polymers, using such polymers as coatings, and generating hydrogen sulfide from such a coating under physiological conditions.

Example 1

Copolymerization of Hexyl Methacrylate/Methacrylamide 9.0 g Hexyl methacrylate, 1.0 g methacrylamide, 80 mg. AIBN, 20 g dioxane, and a stir bar were charged into a 60 mL glass bottle, sealed, and purged with Nitrogen for 30 min. This was put into a 60 degree C. oil bath for 3 hr. The solution was slightly hazy before and after heating, with a small amount of undissolved material at completion. The polymer was precipitated into about 300 mL MeOH, and re-dissolved in about 10 mL DCM. The next two precipitations were done into about 150 mL MeOH, and finally it was dissolved in DCM, and dried on a Teflon sheet. This was first air dried, then put under high vacuum at 40 degrees C. overnight. After drying there was approx. 4 g clear, colorless polymer. The polymer has a glass transition temperature of 29.7° C. and a $M_n$ of 163,589.

Example 2

Preparation of C19 Polymer

C19 is a terpolymer of vinyl acetate, hexyl methacrylate and N-vinylpyrrolidone in the molar ratio of 5:77:18. Its synthesis is describe at least in U.S. Patent Publication 2005/0084515 A1, the contents of which are incorporated by reference herein in its entirety

Example 3

Thiation of C19 Polymer with Lawesson's Reagent

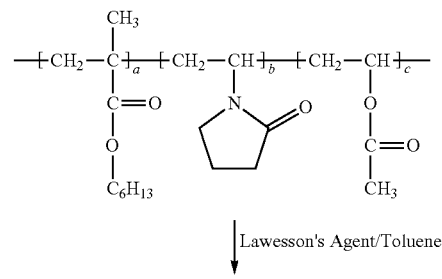

-continued

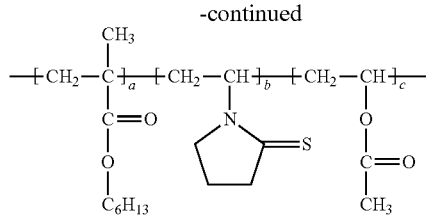

1.0 g terpolymer of vinyl pyrrolidinone, hexyl methacrylate and vinyl acetate (C19 polymer) was dissolved in 10 mL toluene. 0.58 g Lawesson's reagent was quickly weighed out, and added to the solution, along with a stir bar. The bottle was sealed, purged with nitrogen for 30 min and put into a 100 degree C. oil bath overnight. Gradually the Lawesson's reagent mostly dissolved to give a clear, yellow solution, with some insolubles remaining. The reaction solution was filtered through a 1.0 micrometer syringe cellulose acetate butyrate; cellophane; cellulose nitrate; cellulose propionate; cellulose ethers; and carboxymethyl cellulose.

In an exemplary embodiment, the primer coat is parylene applied to a metal stent. Parylene can provide scaffolding on the medical device for other polymers or polymer systems. In such an embodiment, the $H_2S$ generating polymer can be directly applied to the primer layer or to one or more layers applied to the primer layer.

Although it is within the scope of the present disclosure that additional bioactive agents can be useful in treating a plethora of medical conditions, in some exemplary embodiments, the use of a $H_2S$ generating polymer can alleviate the need for additional bioactive agents. The $H_2S$ generating polymers described herein have the effect of providing cardiovascular effects such as, but not limited to, vasodilatation, anti-inflammation and anti-restenosis. Therefore, medical devices incorporating $H_2S$ generating polymers or polymer systems can have the benefit of alleviating the need for supplemental bioactive agents to treat vasoconstriction, inflammation and restenosis. Removing such bioactive agents from a patient's post implantation treatment can help reduce side effects associated with the systemic, or even local, administration of such agents.

Additionally, removing such agents from systemic administration or local delivery from the same medical device can reduce the complexity of the treatment. For example, some bioactive agents may not work well together or may require separate polymer systems in order to achieve controlled release from the implanted device.

In another embodiment the present invention is directed to a method for inhibiting restenosis in a vessel at risk for restenosis comprising the controlled site-specific delivery of a therapeutic dosage of hydrogen sulfide by release from an implantable medical device comprising a hydrogen sulfide generating polymer. In a preferred embodiment the implantable medical device is a vascular stent.

In another embodiment the present invention is directed to a method for inhibiting inflammation in a vessel at risk for inflammation comprising the controlled site-specific delivery of a therapeutic dosage of hydrogen sulfide by release from an implantable medical device comprising a hydrogen sulfide generating polymer. In a preferred embodiment the implantable medical device is a vascular stent.

In another embodiment the present invention is directed to a method for promoting vasodilation in a vessel in need thereof, comprising the controlled site-specific filter, to give a clear, yellow solution. Then, it was precipitated into about 100 mL MeOH, and the polymer dissolved in about 3 mL DCM. Four more precipitations were done into about 35 mL MeOH, and finally it was dissolved in DCM and dried on a Teflon sheet. This was first air dried, then put under high vacuum at 45 degrees C. overnight. After drying, there was approximately 0.6 g slightly opaque, yellow polymer. The glass temperature of the polymer is 18.9° C. and the Mn is 77,696.

Example 4

Thiation of Hexyl Methacrylate/Methacrylamide Copolymer

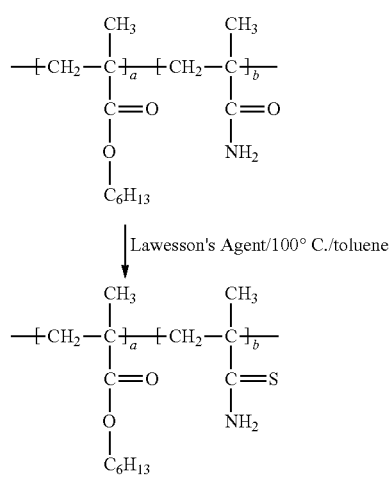

1.0 g copolymer from Example 1 was dissolved in 10 mL toluene. 0.86 g Lawesson's reagent was quickly weighed out, and added to the solution, along with a stir bar. This was sealed, and purged with nitrogen for 30 min. The bottle was put into a 100 degree C. oil bath overnight. Some of the Lawesson's reagent dissolved, with a fair amount remaining un-dissolved at the conclusion. After cooling, it was filtered through a 0.4 micrometer syringe filter. This was precipitated into about 50 mL MeOH, and the polymer dissolved in about 4 mL DCM. Two more precipitations were done into about 40 mL MeOH, and finally it was dissolved in DCM and dried on a Teflon sheet. This was air dried, then put under high vacuum at 45 degrees C. overnight. The polymer has a glass transition temperature of 10.2° C.

Example 5

A piece of thioamide polymer from Example 3 was dip coated onto a metal coupon and incubated in PBS (pH=7.4) in a reaction tube at 37 C for 20 minutes. The generated $H_2S$ gas was purged with argon gas to a chemiluminescence detector for 30 seconds. The positive signal was generated compared to baseline, indicating generation of $H_2S$, as shown in FIG. 1. FIG. 1 is a chemiluminescence graph illustrating release of $H_2S$ over time.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

What is claimed is:

1. An implantable medical device comprising a hydrogen sulfide generating polymer comprising at least one thioamide group and one or more additional monomer units selected from the group consisting of methyl methacrylate, butyl methacrylate, hexyl methacrylate, ethyl methacrylate, 2-ethoxyethyl methacrylate, methyl acrylate, ethyl acrylate, hexyl acrylate and butyl acrylate.

2. The implantable medical device of claim 1 selected from the group consisting of stents, catheters, micro-particles, probes, vascular grafts, and combinations thereof.

3. The implantable medical device of claim 2 that is a vascular stent.

4. The implantable medical device of claim 1 wherein said hydrogen sulfide generating polymer is present as a coating.

5. The implantable medical device of claim 4 further comprising a primer coat.

6. The implantable medical device of claim 4 further comprising a cap coat.

7. An implantable medical device comprising a hydrogen sulfide generating polymer having the formula

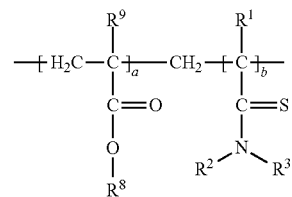

wherein $R^1$ and $R^9$ are each methyl, $R^2$ and $R^3$ are each hydrogen, $R^8$ is n-hexyl, and a and b are each independently an integer of from 1 to 5,000.

8. An implantable medical device comprising a hydrogen sulfide generating polymer having the formula

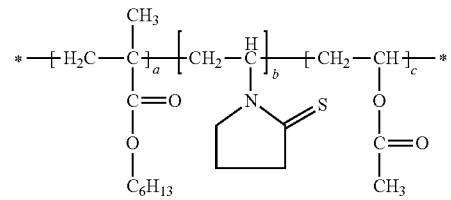

wherein a, b and c are each independently an integer of from 1 to 5,000.

9. A method for inhibiting restenosis in a vessel at risk for restenosis comprising the controlled site-specific delivery of a therapeutic dosage of hydrogen sulfide by release from an implantable medical device of claim 1.

10. A method for inhibiting inflammation in a vessel at risk for inflammation comprising the controlled site-specific delivery of a therapeutic dosage of hydrogen sulfide by release from an implantable medical device of claim 1.

11. A method for promoting vasodilation in a vessel in need thereof comprising the controlled site-specific delivery of a therapeutic dosage of hydrogen sulfide by release from an implantable medical device of claim 1.

12. The method of claim 9 wherein the implantable medical device is a vascular stent.

13. The method of claim 10 wherein the implantable medical device is a vascular stent.

14. The method of claim 11 wherein the implantable medical device is a vascular stent.

\* \* \* \* \*